United States Patent [19]
Yafuso et al.

[11] Patent Number: 4,919,891
[45] Date of Patent: Apr. 24, 1990

[54] SENSOR WITH OVERCOATING AND PROCESS FOR MAKING SAME

[75] Inventors: Masao Yafuso, El Toro; Henry K. Hui; Cheng F. Yan, both of Irvine; William W. Miller, Santa Ana, all of Calif.

[73] Assignee: Minnesota Mining and Manufacturing Company, St. Paul, Minn.

[21] Appl. No.: 49,844

[22] Filed: May 15, 1987

Related U.S. Application Data

[63] Continuation-in-part of Ser. No. 853,460, Apr. 18, 1986, abandoned, and a continuation-in-part of Ser. No. 917,912, Oct. 10, 1986, Pat. No. 4,824,789, and a continuation-in-part of Ser. No. 917,913, Oct. 10, 1986, Pat. No. 4,798,738.

[51] Int. Cl.$^5$ ............................................. G01N 21/64
[52] U.S. Cl. ...................... 422/58; 128/642; 250/227; 350/96.3; 350/96.33; 356/39; 422/82.05; 422/82.08; 422/82.09; 427/2; 436/68; 436/167
[58] Field of Search ...................... 422/58, 68; 436/68, 436/167; 250/227; 356/39; 128/642; 427/2; 350/96.29, 96.3, 96.33

[56] References Cited

U.S. PATENT DOCUMENTS 4,682,895 7/1987 Costello ........................... 422/58 X Primary Examiner—Barry S. Richman
Assistant Examiner—Jill Johnston
Attorney, Agent, or Firm—Donald M. Sell; Walter N. Kirn; Dale E. Hulse

[57] ABSTRACT

A sensor comprising a sensing element capable of sensing a component in an aqueous medium and an overcoating at least partially covering the sensing element. The overcoating comprises a water insoluble, component permeable, cross-linked cellulosic material and an effective amount of an opaque agent.

39 Claims, 1 Drawing Sheet

SENSOR WITH OVERCOATING AND PROCESS FOR MAKING SAME

CROSS REFERENCE TO RELATED APPLICATION

This application is a continuation in part of U.S. patent application Ser. No. 853,460, filed Apr. 18, 1986, and now abandoned, entitled, "Optical Sensor"; U.S. patent application Ser. No. 917,913, filed Oct. 10, 1986, now U.S. Pat. No. 4,798,738, entitled, "Improved Microsensor"; and U.S. patent application Ser. No. 917,912, filed Oct. 10, 1986, entitled, "Improved Gas Sensor". The entire disclosure of each of these applications is herein incorporated by reference.

BACKGROUND OF INVENTION

This invention is directed to overcoatings for sensors and processes for preparing these overcoated sensors.

In the above-mentioned patent applications there are described certain sensors and/or sensing systems for determining blood constituents. Typically of interest would be the determination of the concentration of gases (partial pressure of gases), such as oxygen and carbon dioxide, of hydrogen ions (pH), of other electrolytes, of glucose and the like in the blood. These provide useful parameters for assessment of certain physiological conditions of a patient.

The above-noted patent applications provide teachings for the construction of "sensors". These sensors are preferably of a sufficiently small size to be used directly in vivo in a patient. This contributes to monitoring the condition of the patient on a continuous basis, as opposed to older known procedures which required the extraction of a blood sample for determination in a laboratory of the constituents of interest in the blood.

Certain of the sensors of these patent applications utilize optical indicators, in particular fluorescence indicators, having an optical surface. Typically, a matrix material containing a fluorescent dye is loaded onto the optical surface of an optical fiber. Interaction of the dye with the component to be sensed is monitored utilizing optical signals carried by the optical fibers.

It would be advantageous to provide a durable sensor which has no substantial or significant detrimental effect of the patient being monitored.

SUMMARY OF THE INVENTION

This invention provides for overcoated sensors, probes which includes a plurality or a bundle of sensors which are overcoated, and processes for preparing the same. The sensors including the overcoatings are effective, often more effective and useful because of the inclusion of the overcoatings.

This can advantageously be achieved in a coating for a sensing element which includes a water insoluble component permeable, cross-linked cellulosic material and an effective amount of an opaque agent. By "component permeable" is meant that the overcoating is permeable to the component which is being sensed by the sensing element of the sensor.

The opaque agent can be distributed throughout the overcoating or the opaque agent can be placed on the sensing element and covered with the overcoating.

The present sensor includes a sensing element capable of sensing a component in an aqueous medium. The sensing element may be of conventional and well known design and construction. Sensing elements disclosed in the above-noted patent applications are useful in the present invention. Preferably, the sensing element is chosen from optical indicators and electro-chemical indicators, with the optical indicators being particularly useful. The useful optical indicators include both fluorescence indicators and absorbance indicators, with the fluorescence indicators being especially useful.

The optical indicators function by modifying a light signal, e.g., in an optical fiber, in response to the presence of a certain component, e.g., in an aqueous medium. For example, fluorescence indicators often include a de which is sensitive or responsive to a component. This dye can be placed on the tip of an optical fiber and exposed to the aqueous medium containing the component of interest. By monitoring the light signals from the dye tipped optical fiber, the concentration or partial pressure of the component in the aqueous medium can be determined.

Any aqueous medium may be analyzed using the present sensors or probes. However, the present system is particularly useful for analyzing biological or bodily fluids, such as blood, saliva and the like in vivo, e.g., in a human health care patient. The system is especially useful in analyzing blood.

One important feature of the present overcoating is that of strength or durability. For example, if, as is preferred, the present sensor o probe is to be placed in the cardiovascular system of a human patient to monitor one or more components in the patient's blood, the overcoating should have sufficient strength to remain in tact during such service. On the other hand, the overcoating is to be permeable to the component or components being sensed by the sensing element or elements to allow the component or components of interest to access the sensing element or elements.

Cellulose-containing overcoatings are water insoluble and have a degree of both strength and permeability. However, improvements in at least one, preferably both, of these properties would be highly beneficial.

It has been found that an overcoating containing a crosslinked cellulose material has useful strength properties. Sensors and probes with such overcoatings are useful in the above-noted in vivo blood analysis service. The component permeability of the cross-linked cellulose containing overcoating can be advantageously affected by using one or more permeability enhancing agents during the formation of the overcoating, as is described.

The overcoated sensors of the present invention can be used to sense any suitable component is an aqueous medium. Such components include, for example, gases, hydrogen ions, other electrolytes and glucose. Gases, such as oxygen and carbon dioxide, and hydrogen ions (often represented by pH) are very suitable to be analyzed or monitored by the present system, particularly when the aqueous medium is blood.

Opaque agents are useful in the present invention to perform one or more of the following: provide beneficial sensing element isolation; and reduce fluorescent dye migration into the sensing element.

When fluorescent dyes are employed, it is preferred to select the opaque agent from dye adsorptive opaque agents and dye non-adsorptive opaque agents. By "dye adsorptive opaque agents" is meant those agents which are capable of physically absorbing or adsorbing one or more of the fluorescent dyes used in a given sensor or probe. Examples of dye adsorptive opaque agents include carbon black, other carbon based opaque agents, and the like and mixtures thereof. Carbon black is a particularly useful dye adsorptive opaque agent. By "dye non-adsorptive opaque agents" is meant those agents which are substantially not capable of physically absorbing or adsorbing one or more of the fluorescent dyes used in a given sensor or probe. Examples of dye non-adsorptive opaque agents include ferric oxide, metallic phthalocyanines and mixtures thereof. Included among the metallic phthalocyanines useful in the present invention as opaque agents are phthalocyanines of the following metals: copper, iron, cobalt, lithium, magnesium, nickel, zinc, vanadium, manganese, sodium and mixtures thereof. A particularly useful dye non-adsorptive opaque agent is copper phthalocyanine.

The present invention further involves a process for forming an overcoating of a coating material on a sensing element. In this process, the sensing element is contacted with a composition containing a solvent and a soluble (in the solvent) cellulosic coating material or a soluble (in the solvent) precursor of a cellulosic coating material to form a composition coated sensing element. The composition coated sensing element is treated, e.g., as discussed hereinafter, to form or generate a cellulosic material-containing overcoating on the sensing element. The use of soluble cellulosic coating materials or soluble precursors thereof allows for control of the amount of composition coated onto the sensing element and for a uniform and strong overcoating.

In one embodiment both the composition and the overcoating include an opaque agent. At least a portion of the opaque agent can be coated onto the sensing element before the sensing element is contacted with the composition. In this embodiment, the present process further comprises contacting the sensing element with an opaque agent to at least partially coat the sensing element with the opaque agent prior to contacting the sensing element with the composition.

The composition preferably further includes at least one additional component in an amount effective to enhance the permeability (component permeability) of the overcoating. The additional component is preferably removed from the overcoating during the treating phase of the present process, e.g., by an aqueous wash. Thus, the presently useful permeability enhancing agents are preferably water soluble or are made water soluble while the overcoating itself is water insoluble. These permeability enhancing agents preferably have no substantial detrimental effect on the cross-linked cellulosic coating material, on the sensing element and on the opaque agent. Preferably, the permeability enhancing agent remains substantially unaffected during the present process until it is removed to leave a more permeable overcoating relative to an overcoating produced without the permeability enhancing agent.

Any suitable permeability enhancing agent may be employed. Preferably, the permeability enhancing agent is soluble in the solvent used in the composition. This results in an overcoating with substantially uniform component permeability. Particularly useful permeability enhancing agents are acylated glycerol and sugars, e.g., sucrose, in which the acyl groups contain about 1 to about 10 carbon atoms and mixtures thereof. Acetylated sucrose, e.g., sucrose octaacetate, and glycerol triacetate are examples of these preferred permeability enhancing agents.

Although the cellulosic coating material itself may be included in the composition, it is preferred to use one or more soluble precursors of such cellulosic materials. Such precursors should be soluble in the solvent used in the composition and, during the treating phase of the present process, convert into a portion of the cross-linked cellulosic material-containing overcoating. One particularly useful class of cellulosic material precursors is the acylated celluloses in which the acyl groups include about 1 to about 10 carbon atoms. Acetylated cellulose or cellulose acetate is a particularly useful cellulosic material precursor.

The solvent used in the composition is chosen to allow the cellulosic material or cellulosic material precursor to be soluble in the composition. This solvent is preferably nonaqueous, more preferably organic, in nature. Oxygen-containing hydrocarbon solvents such as ketones, ethers and aldehydes can be used advantageously. Acetone is particularly useful.

The treating phase or step of the present process preferably is effective to cross-link the cellulosic material. In one embodiment, the treating acts to form the overcoating by hydrolyzing the cellulosic material or precursor thereof and cross-linking this hydrolyzed material or precursor. Such a treating sequence is particularly effective when the composition contains a cellulosic material precursor.

The term "cross-linking" as used herein refers to a chemical reaction in which cellulosic molecules are reacted with multi-functional, e.g., difunctional, compounds to join the cellulosic molecules together by bridges or cross-links derived from the multi-functional compounds or cross-linking agents. Hydrolyzing, the cellulosic material or precursor, e.g., using conventional techniques, makes the material or precursor more amenable to being cross-linked. Suitable cross-linking agents for use in the present invention include ethylene glycol diglycidyl ether, butanediol diglycidyl ether, epichlorohydrin, 1,3, butadiene diepoxide, 1,2,7,8 - diepoxy octane, 1,2,5,6-diepoxy cyclooctane, diethylene glycol diglycidyl ether, other poly (i.e., di, tri, etc.) epoxides and mixtures thereof. Ethylene glycol diglycidyl ether is a particularly useful cross-linking agent.

In another broad aspect, the present invention is directed to a probe which comprises a plurality of sensing elements each of which is capable of sensing a different component in an aqueous medium. A plurality of first overcoatings are included, each of which is located on a different sensing element. These first overcoatings contain a water insoluble, component permeable, cross-linked cellulosic material and an effective amount of a first opaque agent. In addition, a second overcoating is provided and is located on all of the first overcoated sensing elements. Preferably, the tips of the first overcoated sensing elements are substantially free of the second overcoating. This second overcoating includes a water insoluble, all component permeable, cross-linked cellulosic material, and preferably an effective amount of a second opaque agent. By "all component permeable" is meant that the second overcoating is permeable to all components of interest, i.e., to all components being sensed by the sensing elements is the probe, in the aqueous medium. This second overcoating provides additional strength to the probe and acts to make the probe physically more smooth.

The final overcoating, whether it is the overcoating on a single sensing element if no second overcoating is applied or the second overcoating on a bundle of sensors each of which contain a first overcoating, preferably has a blood compatible film formed on it. This film, which is often composed of an antithrombogenic agent, acts to inhibit adverse effects of having the sensor or probe in the blood stream.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

This invention will be better understood when taken in conjunction with the drawings wherein.

DETAILED DESCRIPTION OF THE INVENTION

Figure 1:
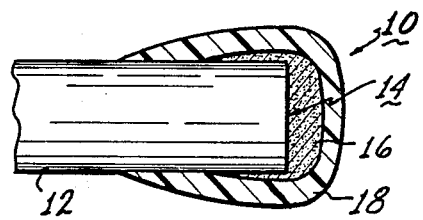
FIG. 1 is a side elevational view in section of a first sensor, including an overcoating of this invention.

The above-noted patent applications all describe optical sensors and components utilized with these sensors to measure the concentration or partial pressure of a given component, in an aqueous medium, such as blood. Each of these sensors utilizes an optical indicator of the fluorescent dye type which is held in position on an optical surface of an optical fiber. When the component to be sensed contacts or interacts with an optical indicator, an optical signal is generated which is correlatable to the amount of the component which is present.

In the illustrative embodiments of the above-noted patent applications certain fluorescent dyes are utilized.

The fluorescent dye of each individual sensing element is preferably combined with a suitable matrix and/or other carrier. Thus, for instance, in the above-noted patent applications a dye solubilized in a siloxane matrix is utilized for oxygen partial pressure-sensing; a dye attached to a cellulose matrix is utilized for pH-sensing measurement; and a dye solubilized in aqueous microcompartments suspended in a siloxane matrix is utilized for carbon dioxide partial pressure-sensing. Each of these systems places the dye on the optical surface of an optical fiber. An excitation signal is fed through the optical fiber to the dye and a fluorescent signal emitted from the dye in response to interaction of the dye with the component of interest is carried by the optical fiber from the dye to suitable analyzing instrumentation. The sensors can be sized to be of the size domain of the optical fiber itself.

Each of the above sensors can be advantageously augmented by including an appropriate overcoating on the sensing element, i.e., the fluorescent dye. The overcoating enhances the performance of the sensors in several ways. It can serve as a protective membrane over these sensors to isolate the optical indicators from the environment which is being sensed, for instance, the blood. Further it can serve to optically isolate the sensor from that environment or from a second sensor located in the vicinity of a first sensor. Additionally, it can provide a suitable surface on which further material can be located, for example, a film of antithrombogenic material. Also, it provides for an essentially smooth outer surface on the sensor which inhibits thrombogenic reaction of the blood to the sensor. The overcoating of the sensor is permeable to the component being sensed. The overcoating is insoluble in the aqueous medium, e.g., blood or other biological or bodily fluids, being tested so as to not contaminate the aqueous medium being tested.

To enhance certain operating characteristics of the sensors, the overcoating includes an opaque agent effective to optically isolate the sensing element from the environment. This opaque agent can be suspended directly in the overcoating material whereby the totality of the overcoating material itself becomes opaque, or the opaque agent can be placed on the surface of the sensing element in a suitable carrier, with the overcoating material being placed over the opaque agent.

The overcoating can be formed as a single layer or as multiple layers which are built up one on the other. It is generally preferred to keep the overcoating material of a thickness sufficient to provide for proper functioning of the overcoating as per the parameters outlined herein, but not of such a thickness as to substantially inhibit transfer of the component species through the overcoating material in the time frame for use of the sensor. Typically, the sensor should equilibrate with the aqueous medium being tested within a few minutes time, and as such, generally the overcoating material will be relatively thin so as to allow for equilibration within this time frame.

In one embodiment, a permeability enhancing agent is preferably utilized in producing the overcoated sensors and probes of the present invention. For example, the permeability enhancing agent may be included in solution with a soluble coating material or a soluble precursor of a coating material in a composition which is contacted with and coats the sensing element or elements. The permeability enhancing agent is preferably later removed from the overcoating, e.g., by washing with an aqueous wash medium. Typically, the permeability enhancing agent will be a water soluble compound, or be converted into a water-soluble compound as for instance a compound having one or more hydroxyl groups, such as a poly-hydroxyl compound.

Multiple overcoatings can be utilized, as for instance a first overcoating which serves in part, to hold an opaque agent in association with a sensor, and a second overcoating which serves in part, to provide for a smooth surface over a probe or bundle of sensors grouped together. The second overcoating may or may not include an opaque agent, although it is preferred to include an opaque agent since this aids in manufacturing the present devices.

When a probe. i.e., a plurality or a bundle of sensors, is utilized, it is desirable to eliminate "cross talk" between the individual sensors. That is, it is desirable to inhibit signals, e.g., optical signals, from one sensor influencing the signals of a second sensor. By providing an individual overcoating on each sensor prior to forming the bundle of sensors, cross talk between the sensors can be substantially reduced or even eliminated. The bundle of microsensors can then be coated with a final overcoating to provide a substantially smooth and uniform surface. The tip of each of the individual sensors is preferably not coated with the final overcoating.

The overcoating of the present sensors and probes comprises a water insoluble, component permeable, cross-linked cellulosic material. The material is permeable to a component to be sensed.

To facilitate formation of the cellulosic material containing overcoating, a composition including an organic solvent and an organic solvent soluble precursor of cellulose, as for instance carboxylated cellulose, is preferably utilized. Acetylated cellulose can be conveniently solvated in acetone. The acetone composition can be easily and conveniently applied to the sensing element by simply depositing a microdroplet of the composition on the tip of the sensor and allowing the acetone to evaporate.

The cellulosic material or precursor thereof is preferably then strengthened by cross-linking. When acetylated cellulose is utilized as a cellulosic material precursor in forming a overcoating, the acetyl groups can be concurrently removed from the acetylated cellulose during cross-linking by conducting a combination hydrolysis/cross-linking reaction.

Preferred permeability enhancing agents are the acetylated polyols, glycerol and sucrose. This acetylated polyols are also soluble in organic solvents, such as acetone. During the hydrolysis reaction of the cellulosic material on the sensing element, the acetylated polyol is also hydrolyzed, allowing for removal of the polyol by elution into the aqueous treatment medium. Since the cellulose is not water soluble, when the polyol contained in the cellulose is exposed to an aqueous wash, the polyol dissolves into the aqueous wash leaving behind a more permeable cellulose matrix of the overcoating material.

If a substituted precursor of the cross-linked cellulosic material is utilized, as for instance acetylated cellulose, the substituent groups are preferably removed, e.g., before or at the time of the cross-linking. With acetylated cellulose, the acetyl substituent groups can be removed in a facile manner with the use of a dilute basic solution. Thus, for instance, a 1% sodium hydroxide solution can be used. If an acetylated permeability enhancing agent, such as glycerol triacetate, is also utilized, concurrently with the hydrolysis of the acetyl groups of the cellulose, the acetyl groups of the glycerol triacetate are also hydrolyzed. Cross-linking of the resulting cellulosic matrix can be carried out sequentially, e.g., after, or concurrently with this hydrolysis.

Typically, the cellulose acetate is utilized as a mixture of di- and tri- acetyl cellulose. Such a mixture is commercially available and has increased solubility is acetone compared to neat triacetylated cellulose.

The opaque agent is selected to be opaque to the particular wavelength or wavelengths of light at which the sensor operates. These are selected depending upon the characteristics of the sensor as, for instance, the particular dye utilized in the sensor.

Dye adsorptive opaque agents, such as carbon black and the like, are particularly suitable for use in an opaque agent in certain sensors such as the carbon dioxide sensor because of such agent's ability to block a broad band of optical wave lengths and to prevent the migration of unwanted solvent soluble dyes from adjacent sensing elements during the overcoating process. An example is the prevention of the migration of the oxygen dye into the carbon dioxide sensor during the overcoating process.

In a sensor, that has a sensing dye that is soluble in the composition used to coat the sensing element, a dye nonadsorptive opaque agent is used since carbon black can cause depletion of the sensing dye from the sensor by dye extraction during the overcoating process. Copper phthalocyanine is a particularly effective dye nonadsorptive opaque agent in the cellulosic overcoating composition for the oxygen sensing element employing a fluorescent dye and for a bundle of sensors that contain such an oxygen sensing element.

The opaque agent, when used as a mixture with the coating material, is suitably suspended in the composition used to coat the sensing element, for example, utilizing a suitable homogenizer or the like. Thus, carbon black or copper phthalocyanine can be directly suspended in the composition containing the soluble cellulosic material or soluble precursor, and when the cellulosic material is cross linked, the carbon black or copper phthalocynine is permanently dispersed and held throughout the totality of the matrix of the overcoating.

The Figures show several embodiments of sensors which incorporate overcoatings in accordance with this invention. For the purposes of describing these figures, the actual fluorescent dye in a suitable matrix is referred to as a sensing element. Details as to the preparation of these sensing elements is described in the above-noted patent applications.

In FIG. 1 a first sensor 10 is shown. Sensor 10 includes an optical fiber 12 having an optical surface 14. Positioned directly against optical surface 14 and down along the sides of the tip of optical fiber 12 is a sensing element 16. Covering sensing element 16 is an overcoating 18. The overcoat 18 extends completely over sensing element 16 and down along the side of optical fiber 12. Thus, the totality of sensing element 16 is completely covered by overcoating 18. Sensor 10 of FIG. 1 is typically utilized as a pH sensor as is described in patent application Ser. No. 917,912 noted above.

Overcoating 18 of sensor 10 includes carbon black (not separately shown or numbered) dispersed within the matrix of overcoating 18. Because overcoating 18 completely surrounds sensing element 16, sensing element 16 has an opaque coating completely around it. This optically isolates sensing element 16 from the optical environment outside of overcoating 18.

Figure 2:
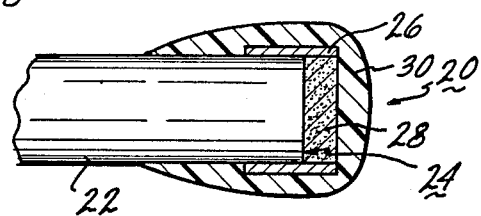
FIG. 2 is a side elevational view in section of a second sensor including an overcoating of this invention.

In FIG. 2 a second sensor 20 is illustrated. It includes an optical fiber 22 having an optical surface 24. Positioned on the end of optical fiber 22 is a sleeve 26 which holds an aliquot of a polymerized matrix containing sensing element 28 against optical surface 24. An overcoating 30, having an opaque agent located therein, completely covers sensing element 28 and sleeve 26. Sensor 20, having overcoating 30 thereon is used as either a carbon dioxide sensor or an oxygen sensor as described in above-noted U.S. patent application Ser. No. 917,913. In the case of the carbon dioxide sensor, the preferred opaque agent is carbon black. In the case of the oxygen sensor, the preferred opaque agent is copper phthalocyanine.

Figure 3:
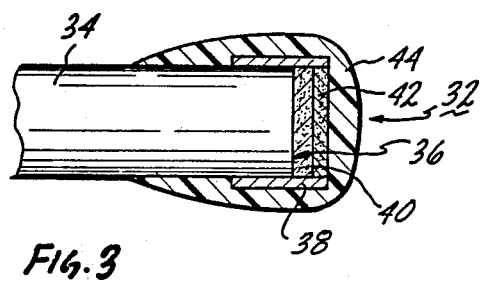
FIG. 3 is a side elevational view in section of a third sensor including an overcoating of this invention.

In FIG. 3 a third sensor 32 is illustrated. It is similar to sensor 20 of FIG. 2. It includes an optical fiber 34 having an optical surface 36 thereon. A sleeve 38 is utilized to hold an aliquot of a sensing element 40 against optical surface 36.

Sensor 32 differs from sensor 20 in that an opaque layer 42 is overlayed on sensing element 40. Opaque layer 42 is preferably formed of dimethylpolysiloxane having an opaque agent, such as ferric oxide, dispersed therein. An overcoating 44 is now located over the totality of the end of optical fiber 34, sleeve 38 and opaque layer 42. Since sensing element 40 is optically isolated by opaque layer 42, overcoating 44 can be formed as a transparent layer. Alternatively, overcoating 44 can also include an opaque agent.

Figure 4:
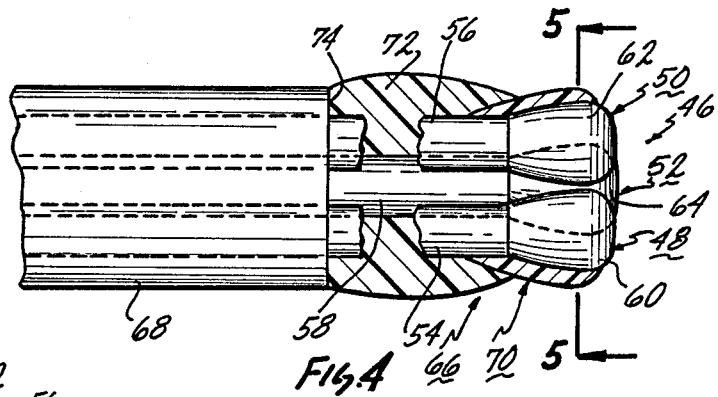
FIG. 4 is a side elevational view partially broken away, showing a composite bundle of overcoated sensors.
Figure 5:
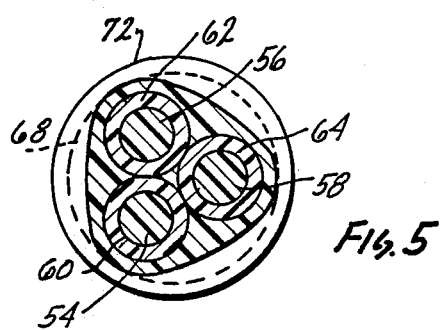
FIG. 5 is an end elevational view in section about the lines 5—5 of FIG. 4.

FIGS. 4 and 5 show a sensor probe or bundle of individual sensors grouped together. Thus, in FIGS. 4 and 5 a sensor bundle 46 is shown. It includes three sensors, sensor 48, sensor 50 and sensor 52. These can be chosen to be one of any of the sensors shown in FIGS. 1, 2 and 3, or other sensors as might be desired for a particular application. In view of this, explicit details of these sensors are not shown. They each however include suitable optical fibers, 54, 56 and 58, respectively. Located on each of these optical fibers and covering the specific components of the specific sensors 48, 50 and 52 are individual overcoatings 60, 62 and 64. Each of overcoatings 60, 62 and 64 include an opaque agent either in the overcoating material or another opaque agent such as sensor 32 of FIG. 3, such that individual sensors 48, 50 and 52 are optically isolated from one another to eliminate cross talk between these sensors.

Sensors 48, 50, 52 are located together at the bundle tip 66 of sensor bundle 46. Optical fibers 54, 56 and 58 are arranged in a triangular arrangement as is evident from FIG. 5. Fibers 54, 56 and 58 are held together by a sleeve 68. Sleeve 68 is utilized to assist in introduction of sensor bundle 46 into its working environment, as for instance intravenous positioning of sensor bundle 46.

Individual sensors 48, 50 and 52, having individual overcoating 60, 62, and 64, are positioned within sleeve 68 and a final bundle overcoating 70 is then applied along the sides of bundle tip 66 without coating the end of bundle tip 66. Bundle overcoating 70 fills in the voids between individual overcoatings 60, 62, and 64 forming a smooth surface at bundle tip 66 which inhibits thrombogenic reaction to sensor bundle 46. An epoxy coating 72 is positioned on sensor bundle 46 between the end 74 of sleeve 68 and bundle overcoating 70.

As is evident from FIG. 4 bundle overcoating 70 forms a smooth transition with epoxy coating 72 to sleeve 68. This substantially eliminates any pockets or voids that could provide a region of stasis where blood could coagulate. Finally, sensor bundle 46 is covered with a blood compatible coating of a antithrombogenic agent (not shown in the drawings) that extends along the entire length of the bundle.

The following representative, non-limiting examples illustrate certain aspects of the present invention.

EXAMPLE 1

10 grams of acid free cellulose acetate available from Kodak Chemicals, Rochester, NY, having 39.9% acetyl content was dissolved in 100 grams of anhydrous acetone.

EXAMPLE 2

To 10 grams of 10% cellulose acetate/acetone solution of Example 1, above, was added 0.2 grams of acid-free sucrose ocataacetate, available from Sigma Chemicals, St. Louis, MO, and 0.4 grams of copper phthalocyanine available from Aldrich Chemical Co., Milwaukee, WI. The mixture was homogenized in a Virtis 45 high shear homogenizer for five minutes with the container positioned in a water bath for cooling during homogenization.

EXAMPLE 3

10 grams of acid-free sucrose ocataacetate was dissolved in 100 grams of anhydrous acetone.

EXAMPLE 4

A thin layer of the cellulose acetate/sucrose octaacetate/copper phthalocyanine mixture from Example 2, above, was applied to the end of the oxygen sensor equivalent to sensor 20, above. The coating mixture was transferred to the sensor utilizing a tiny rod as a carrier. The rod was dipped into the cellulose acetate/sucrose octaacetate/copper phthalocyanine mixture to adhere a microdroplet of this mixture on the end of the rod. The end of the rod was then dipped into the sucrose octaacetate/acetone solution of Example 3 to further wet the microdrop just prior to application to the sensor to minimize the effect of evaporation before and during the application process. After the coating was applied, the solvent was allowed to evaporate. The overcoating was then hydrolyzed and cross-linked by immersion in an aqueous solution containing 1.0% by weight sodium hydroxide and 5% by weight ethylene glycol diglycidyl ether for thirty minutes. After hydrolysis and cross-linking, the overcoated sensor was rinsed in an aqueous solution containing 1% by weight sodium bicarbonate and 5% by weight glycerol.

EXAMPLE 5

To 10 grams of the 10% by weight cellulose acetate/acetone solution of Example 1 was added 0.4 grams of carbon black. The mixture was homogenized as in Example 2, and applied to a carbon dioxide sensor, hydrolyzed and cross-linked as in Example 4. The sensor is rinsed as in Example 4.

EXAMPLE 6

In a like manner to Example 4, an overcoating was applied to a pH sensor similar to sensor 10, above, except that the overcoating composition contained 4% by weight carbon black instead of copper phthalocyanine and 10% by weight triacetin instead of sucrose octaactate. In addition, the acetone resolvation solution contained triacetin instead of sucrose octaacetate.

EXAMPLE 7

In a like manner to Example 6, an overcoating was applied to the pH sensor similar to sensor 10, above, except that the hydrolysis and cross-linking steps were carried out separately. First the overcoat was hydrolyzed by immersion in a 1% by weight sodium hydroxide aqueous solution. Then it was cross-linked by immersion in an aqueous solution containing 1.0% by weight of sodium hydroxide and 5% by weight of ethylene glycol diglycidyl ether.

EXAMPLE 8

Example 4 with a further overcoating of cellulose acetate utilizing the cellulose/sucrose octaacetate solution prepared as per Example 2, with the exception that copper pythalocyanine was omitted. After application of the cellulose acetate/acetone solution to the oxygen sensor, the acetone was allowed to evaporate and the cellulose acetate was then hydrolyzed and cross linked as per Example 6, above.

EXAMPLE 9

A carbon dioxide sensor, an oxygen sensor and a pH sensor were combined in a sleeve so as to locate the sensors together in a bundle. Using the mixture of Example 2 and the procedure of Example 4, a thin overcoating was applied on the side of the bundle. Care was taken to prevent buildup of the overcoating at the bundle tip in order to hold the overcoating thickness at the tip to a minimum. However, sufficient coating material was utilized to fill in the spaces between the individual sensors.

EXAMPLE 10

In a like manner to Example 9, an overcoating containing copper phthalocyanine in place of carbon black was formed on a sensor bundle containing an oxygen sensor, a carbon dioxide sensor and a pH sensor.

While the present invention has been described with respect to various specific examples and embodiments, it is to be understood that the present invention is not limited thereto and that it can be variously practiced within the scope of the following claims.

What is claimed is:

1. A sensor comprising a sensing element capable of sensing a component in an aqueous medium and an overcoating at least partially covering said sensing element, said overcoating comprising a water insoluble, component permeable cellulosic material cross-linked with one or more multi-functional cross-linking agents and an effective amount of an opaque agent.

2. The sensor of claim 1 wherein said sensing element is selected from the group consisting of optical indicators and electro-chemical indicators.

3. The sensor of claim 1 wherein, said sensing element is selected from the group consisting of optical indicators.

4. The sensor of claim 1 wherein said sensing element is selected from the group consisting of fluorescence indicators and absorbance indicators.

5. The sensor of claim 1 wherein said sensing element is selected from the group consisting of fluorescence indicators.

6. The sensor of claim 5 wherein said opaque agent is a dye adsorptive opaque agent.

7. The sensor of claim 6 wherein said opaque agent is a dye adsorptive opaque agent and said dye adsorptive opaque agent is carbon black.

8. The sensor of claim 6 wherein said sensing element is a fluorescence indicator capable of sensing carbon dioxide.

9. The sensor of claim 5, wherein said opaque agent is a dye non-adsorptive opaque agent.

10. The sensor of claim 9 wherein said dye non-adsorptive opaque agent is selected from the group consisting of ferric oxide and metallic phthalocyanines.

11. The sensor of claim 10 wherein said dye non-adsorptive opaque agent is a metallic phthalocyanine and the metallic portion of said phthalocyanine is selected from the group consisting of copper, iron, cobalt, lithium, magnesium, nickel, zinc, vanadium, manganese, sodium and mixtures thereof.

12. The sensor of claim 9 wherein said sensing element is a fluorescence indicator capable of sensing oxygen.

13. The sensor of claim 12 wherein said dye non-adsorptive opaque agent is copper phthalocyanine.

14. The sensor of claim 1 wherein said aqueous medium is a bodily fluid.

15. The sensor of claim 14 which further comprises a blood compatible film located on the outside surface of said overcoating.

16. The sensor of claim 1 wherein said aqueous medium is blood.

17. The sensor of claim 1 wherein said cross-linked cellulosic material is cross-linked cellulose.

18. The sensor of claim 1 wherein said component is selected from the group consisting of gases, hydrogen ions, other electrolytes and glucose.

19. The sensor of claim 1 wherein said component is selected from the group consisting of gases and hydrogen ions.

20. The sensor of claim 1 wherein said component is selected from the group consisting of oxygen, carbon dioxide and hydrogen ions.

21. An overcoated sensing element produced in accordance with the process comprising:
contacting a sensing element with a composition containing a solvent and a solvent soluble cellulosic coating material or a solvent soluble precursor of said cellulosic coating material to form a composition coated sensing element; and
treating said composition coated sensing element to form an overcoating on said sensing element, said overcoating being permeable to a component of interest, wherein said composition further includes a permeability enhancing agent in an amount effective to enhance the component permeability of said overcoating formed.

22. An overcoated sensing element as defined in claim 21 wherein said permeability enhancing agent is substantially removed from said composition coated sensing element during said treating step.

23. An overcoated sensing element as defined in claim 22 wherein said permeability enhancing agent is water soluble and said treating step comprises contacting said composition coated sensing element at conditions effective to form a cross-linked cellulosic material on said sensing element and contacting said sensing element containing said cross-linked cellulosic material with an aqueous liquid at conditions effective to substantially remove said permeability enhancing agent.

24. An overcoated sensing element as defined in claim 23 wherein said composition coated sensing element is contacted at conditions effective to hydrolyze at least a portion of said cellulosic material on said sensing element, and said sensing element containing said hydrolyzed cellulosic material is contacted with at least one cross-linking agent at conditions effective to form a cross-linked cellulosic material on said sensing element.

25. A probe capable of sensing a plurality of different components in an aqueous medium which comprises:
a plurality of sensing elements each of which is capable of sensing a different one of said components in said aqueous medium;
a plurality of first overcoatings each of which is located on a different one of said sensing elements and each of which comprises a water insoluble, component permeable cellulosic material cross-linked with one or more multi-functional cross-linking agents and an effective amount of first opaque agent; and
a second overcoating located on all said first overcoated sensing elements and comprising a water insoluble, all component permeable cellulosic material cross-linked with one or more multi-functional across-linking agents.

26. The probe of claim 25 wherein said sensing elements are selected from the group consisting of optical indicators and electro-chemical indicators.

27. The probe of claim 26 wherein said aqueous medium is a bodily fluid.

28. The probe of claim 25 wherein said sensing elements are selected from the group consisting of optical indicators.

29. The probe of claim 25 wherein said sensing elements are selected from the group consisting of fluorescence indicators and absorbance indicators.

30. The probe of claim 25 wherein said sensing elements are selected from the group consisting of fluorescence indicators.

31. The probe of claim 30 wherein each of said first opaque agents is a dye adsorptive opaque agent.

32. The probe of claim 31 wherein said second overcoating further comprises an effective amount of a second opaque agent and wherein said second opaque agent is a dye non-adsorptive opaque agent.

33. The probe of claim 32 wherein said dye adsorptive opaque agent is carbon black and said dye non-adsorptive opaque agent is copper phthalocyanine.

34. The probe of claim 30 wherein each of said first opaque agents is a dye non-adsorptive opaque agent.

35. The probe of claim 25 wherein said second overcoating further comprises an effective amount of a second opaque agent.

36. The probe of claim 25 wherein said aqueous medium is blood.

37. The probe of claim 25 wherein said cross-linked cellulosic material is cross-linked cellulose.

38. The probe of claim 25 wherein said components are selected from the group consisting of gases, hydrogen ions, other electrolytes and glucose.

39. The probe of claim 25 wherein said aqueous medium is blood and said probe further comprises a blood compatible film located on said second overcoating.

* * * * *

UNITED STATES PATENT AND TRADEMARK OFFICE
CERTIFICATE OF CORRECTION

PATENT NO. : 4,919,891
DATED : April 24, 1990
INVENTOR(S) : Masao Yafuso et al.

It is certified that error appears in the above-identified patent and that said Letters Patent is hereby corrected as shown below:

Col. 2, line 12, "de" should be --dye--.

Col. 2, line 27, "o" should be --or--.

Col. 10, line 54, before "Example" insert --The coated oxygen sensor of Example 4 was coated as per--.

Col, 11, Lines 40 and 41, delete "opaque agent is a dye adsorptive opaque agent and said".

Col. 11, line 29, after "wherein" delete the comma.

Col. 11, line 46, after "5" delete the comma.

Col. 11, line 64, delete "14" and insert therefor --16--.

Col. 12, line 63, delete "across-linking" and insert therefor --cross-linking--.

Signed and Sealed this

Thirteenth Day of August, 1991

Attest:

HARRY F. MANBECK, JR.

Attesting Officer

Commissioner of Patents and Trademarks